United States Patent
L'Alloret et al.

(10) Patent No.: US 10,449,126 B2
(45) Date of Patent: Oct. 22, 2019

(54) OIL-IN-WATER EMULSION

(75) Inventors: Florence L'Alloret, Paris (FR); Jean-Thierry Simonnet, Cachan (FR)

(73) Assignee: L'OREAL, Paris (FR)

( * ) Notice: Subject to any disclaimer, the term of this patent is extended or adjusted under 35 U.S.C. 154(b) by 605 days.

(21) Appl. No.: 12/637,803

(22) Filed: Dec. 15, 2009

(65) Prior Publication Data

US 2010/0190740 A1    Jul. 29, 2010

Related U.S. Application Data

(60) Provisional application No. 61/139,734, filed on Dec. 22, 2008.

(30) Foreign Application Priority Data

Dec. 18, 2008 (FR) ...................... 08 58755

(51) Int. Cl.
*A61K 8/02* (2006.01)
*A61K 8/86* (2006.01)
*A61K 8/46* (2006.01)
*A61K 8/06* (2006.01)
*A61K 8/60* (2006.01)
*A61Q 19/00* (2006.01)
*A61Q 5/00* (2006.01)

(52) U.S. Cl.
CPC .............. *A61K 8/0295* (2013.01); *A61K 8/06* (2013.01); *A61K 8/466* (2013.01); *A61K 8/60* (2013.01); *A61K 8/86* (2013.01); *A61Q 5/00* (2013.01); *A61Q 19/00* (2013.01)

(58) Field of Classification Search
CPC .......... A61K 8/06; A61K 8/0295; A61K 8/60; A61Q 19/00; A61Q 5/00
See application file for complete search history.

(56) References Cited

U.S. PATENT DOCUMENTS

| 4,612,331 A * | 9/1986 | Barratt et al. ................ 514/558 |
| 5,658,575 A * | 8/1997 | Ribier et al. .................. 424/401 |
| 5,925,364 A * | 7/1999 | Ribier et al. .................. 424/401 |
| 6,066,328 A * | 5/2000 | Ribier et al. .................. 424/401 |
| 6,416,768 B1 * | 7/2002 | Ravaux et al. ................ 424/401 |
| 2003/0105169 A1 * | 6/2003 | Lennon .......................... 516/53 |
| 2006/0159638 A1 * | 7/2006 | Segura et al. .................. 424/62 |
| 2007/0027034 A1 * | 2/2007 | Tank et al. .................... 504/363 |
| 2010/0284948 A1 * | 11/2010 | Ohrmann et al. .............. 424/59 |

FOREIGN PATENT DOCUMENTS

| EP | 0227012 | * 7/1987 | ............... A61K 7/00 |
| EP | 0 641 557 | 3/1995 | |
| EP | 2 718 021 | 10/1995 | |
| EP | 0 705 593 | 4/1996 | |
| WO | WO2007147904 | * 12/2007 | ............... A61K 8/06 |

OTHER PUBLICATIONS

English language translation of Notice of Reasons for Rejection dated Jul. 6, 2015 in Japanese Patent Application No. 2009-286837.

* cited by examiner

*Primary Examiner* — Rachael E Bredefeld
(74) *Attorney, Agent, or Firm* — Oblon, McClelland, Maier & Neustadt, L.L.P.

(57) ABSTRACT

The present invention relates to a composition in the form of an emulsion of the oil-in-water type formed of oily globules which are each provided with a lamellar liquid crystal coating and which are dispersed in an aqueous phase, wherein it has a pH ranging from 3 to 5.5 and in that it contains at least one lipophilic surface-active agent with an HLB ranging from 2 to 5, at least one hydrophilic surface-active agent with an HLB ranging from 8 to 12 and at least one amphiphilic compound of ionic nature at a pH ranging from 3 to 5.5.

21 Claims, No Drawings

OIL-IN-WATER EMULSION

REFERENCE TO PRIOR APPLICATIONS

This application claims priority to U.S. provisional application Ser. No. 61/139,734, filed Dec. 22, 2008; and to French patent application 08 58755, filed Dec. 18, 2008, both incorporated herein by reference.

FIELD OF THE INVENTION

The present invention relates to a composition in the form of an emulsion of the oil-in-water type. It relates more particularly to a composition in the form of an oil-in-water emulsion formed by oily globules provided with a lamellar liquid crystal coating and dispersed in an aqueous phase. Preferably, the invention emulsion exhibits a pH ranging from 3 to 5.5. The invention also relates to a process for the preparation of such a composition and to its application in the treatment of the skin and keratinous substance.

Additional advantages and other features of the present invention will be set forth in part in the description that follows and in part will become apparent to those having ordinary skill in the art upon examination of the following or may be learned from the practice of the present invention. The advantages of the present invention may be realized and obtained as particularly pointed out in the appended claims. As will be realized, the present invention is capable of other and different embodiments, and its several details are capable of modifications in various obvious respects, all without departing from the present invention. The description is to be regarded as illustrative in nature, and not as restrictive.

BACKGROUND OF THE INVENTION

Numerous cosmetic compositions for the skin in the form of an emulsion exhibit a pH of greater than 6, mainly for reasons of formulation stability. This is because the stability of the emulsions with regard to coalescence is often reinforced using ionic surfactants, which have to be formulated at a pH at least equal to 6 in order to be in the ionized form.

For example, the document EP 0 641 557 describes oil-in-water emulsions formed of oily globules of defined size provided with a lamellar liquid crystal coating and comprising a lipophilic surface-active agent and a hydrophilic surface-active agent. These emulsions comprise a fatty acid in order to improve their stability and this acid, due to its low pKa, has to be formulated at a pH at least equal to 6 in order to be in the ionized form. The document EP 0 705 593 describes oil-in-water emulsions formed of oily globules of defined size provided with a lamellar liquid crystal coating and comprising a lipophilic surface-active agent, a hydrophilic surface-active agent and an ionic amphiphilic compound conferring on the emulsion a pH ranging from 5.5 to 7.5. These amphiphilic compounds do not make it possible to obtain an emulsion at a low pH.

Furthermore, many gelling agents which provide for the stability of the emulsions with regard to creaming or sedimentation are found to be greatly restricted in their gelling properties at a pH of less than 6.

However, attempts are being made to formulate emulsions having a pH of less than 6, in particular for reasons of harmlessness as such a pH is closer to the pH of the skin, itself between 4.5 and 6, and the microbiological protection of formulations exhibiting this pH range is possible with lower levels of preservatives.

In addition, the compositions exhibiting this pH range make it possible to more easily formulate water-soluble active principles in the acid form, such as salicylic acid or hydroxy acids.

It thus appears necessary to have available cosmetic emulsions, particularly cosmetic and dermatologic emulsions, which are stable at a pH ranging from 3 to 5.5 and which exhibit a broad range of textures extending from fluid to cream.

DETAILED DESCRIPTION OF THE PREFERRED EMBODIMENTS

The inventors have discovered that it is possible to achieve the above objectives, and more, by providing a composition in emulsion form comprising a specific surfactant system.

More specifically, a subject-matter of the present invention is a composition in the form of an oil-in-water emulsion formed of oily globules which are each provided with a lamellar liquid crystal coating and which are dispersed in an aqueous phase, the composition comprising at least one lipophilic surface-active agent, at least one hydrophilic surface-active agent and at least one amphiphilic compound of ionic nature at a pH ranging from 3 to 5.5.

Each oily globule of the composition according to the invention is preferably individually coated with a monolamellar layer and with at least one bilamellar layer which are obtained from the lipophilic surface-active agent, from the hydrophilic surface-active agent and from the ionic amphiphilic compound.

The combination of the surfactants and the specific amphiphilic compound makes it possible to produce emulsions exhibiting a low pH while being stable and having a fluid texture.

The invention makes it possible to have available particularly stable emulsions having small droplets of fatty phase coated with a monolamellar layer and with an oligolamellar layer which is extremely thin. Thus, the use of gelling agents, if necessary, can be made in reduced amounts.

Oligolamellar layer is understood to mean a layer comprising from 2 to 5 lipid lamellae (lipid lamella is understood to mean a membrane of lipid bilayer type as described in the field of liposomes, for example).

The mean size of the coated oily globules can in particular be less than 1 micrometer, preferably less than $800 \times 10^{-3}$ microns.

In the present invention, mean size of the oily globules is understood to mean the number-average size of the drops, as measured, for example, using a BI-90 size analyser (Brookhaven Instruments).

"Stable emulsions" is understood to mean emulsions which, after storage at all temperatures between 4° C. and 50° C. for 2 months, do not exhibit any macroscopic change in colour, smell or viscosity, any variation in pH or any variation in microscopic appearance.

The viscosity of the compositions obtained can range from very fluid (spray) to very viscous (cream). The composition of the invention preferably exhibits a viscosity of greater than or equal to 0.1 Pa·s which can range, for example, from 0.1 Pa·s to 100 Pa·s, preferably from 0.1 Pa·s to 10 Pa·s, at a temperature of 25° C., the viscosity being measured using a Rheomat 180 (Lamy) equipped with an MS-R1, MS-R2, MS-R3, MS-R4 or MS-R5 spindle chosen according to the consistency of the composition and rotating at a rotational speed of 200 rev/min.

The compositions according to the invention preferably exhibit a pH ranging from 3 to 5.5, more preferably from 3 to 5 and better from 4 to 5.

Another object of the invention is a method for the treatment of the skin, hair and/or lips, wherein a composition as above described is applied to the skin, hair and/or lips.

The lipophilic and hydrophilic surfactants used in the present invention are nonionic.

Lipophilic Surfactant

Lipophilic surfactant is understood to mean a surfactant having an HLB parameter ranging from 2 to 5. As is well known, HLB (Hydrophilic-Lipophilic Balance) is understood to mean the balance between the size and the strength of the hydrophilic group and the size and the strength of the lipophilic group of the surface-active agent.

The HLB value according to Griffin is defined in J. Soc. Cosm. Chem., 1954 (volume 5), pages 249-256.

The lipophilic surfactants with an HLB ranging from 2 to 5 can be chosen from:
- ethers of polyethylene glycol and of fatty alcohols, in particular of saturated or unsaturated alcohols comprising from 12 to 30 carbon atoms, preferably from 14 to 26 carbon atoms, such as oleyl alcohol, stearyl alcohol or behenyl alcohol, comprising from 1 to 50 oxyethylene (OE) groups, preferably from 1 to 20 oxyethylene groups, such as, for example, the compounds carrying the INCI names steareth-2, beheneth-2 or oleth-2. These polyethylene glycol ethers can comprise from 1 to 10 fatty chains,
- esters of polyethylene glycol and of fatty acids, in particular of saturated or unsaturated fatty acids comprising from 12 to 30 carbon atoms, preferably from 14 to 26 carbon atoms, such as oleic acid or stearic acid, comprising from 1 to 50 oxyethylene (OE) groups, preferably from 1 to 20 oxyethylene groups, such as polyethylene glycol monostearate (INCI name: PEG-2 stearate). These polyethylene glycol esters can be composed of 1 to 10 fatty chains,
- ethers of polyethylene glycol and of fatty alcohols which are glycosylated, in particular of alcohols comprising from 12 to 30 carbon atoms, preferably from 14 to 26 carbon atoms, the ethers comprising from 1 to 10 oxyethylene (OE) groups, preferably from 1 to 5 oxyethylene groups, and from 1 to 10 glycosyl groups,
- esters of polyethylene glycol and of fatty acids which are glycosylated, in particular of fatty acids comprising from 12 to 30 carbon atoms, preferably from 14 to 26 carbon atoms, comprising from 1 to 5 glycosyl groups, it being possible for the esters to comprise from 1 to 5 fatty chains, preferably from 1 to 5 oxyethylene groups,
- ethers of oxyethylenated alcohols comprising from 12 to 30 carbon atoms, preferably from 14 to 22 carbon atoms, and of glycerol or of polyglycerol, the ethers comprising from 1 to 5 glycerol groups and it being possible for the ethers to comprise from 2 to 10 fatty chains and from 1 to 10 oxyethylene groups,
- esters of fatty acids comprising from 12 to 30 carbon atoms, better still from 14 to 20 carbon atoms (such as stearic acid or behenic acid), and of glycerol or of polyglycerol, the esters comprising from 1 to 10 glycerol groups, such as, for example, diglyceryl distearate, tetraglyceryl tristearate, decaglyceryl decastearate, diglyceryl monostearate, hexaglyceryl tristearate, decaglyceryl pentastearate, the ester of glycerol and of palmitic and stearic acids, and glyceryl mono- and dibehenate,
- esters of sucrose and of fatty acids comprising from 12 to 30 carbon atoms, in particular from 14 to 20 carbon atoms, it being possible for the esters to comprise from 2 to 5 fatty chains, such as, for example, sucrose distearate or sucrose tristearate,
- esters of pentaerythritol and of fatty acids comprising from 12 to 30 carbon atoms, preferably from 14 to 20 carbon atoms, such as, for example, pentaerythritol tetrastearate,
- esters of sorbitol and/or of sorbitan and of fatty acids comprising from 12 to 30 carbon atoms, preferably from 12 to 20 carbon atoms, such as stearic acid, such as, for example, sorbitan monostearate or sorbitan tristearate,
- ethers of polyethylene glycol and of cholesterol comprising from 1 to 10 oxyethylene groups, such as choleth-3, and their mixtures.

Ester is understood to mean a mono- or a polyester.

The lipophilic surfactants are advantageously chosen from steareth-2, beheneth-2, oleth-2, sucrose distearate, sucrose tristearate, diglyceryl distearate, tetraglyceryl tristearate, decaglyceryl decastearate, diglyceryl monostearate, hexaglyceryl tristearate, decaglyceryl pentastearate, sorbitan monostearate, sorbitan tristearate, diethylene glycol monostearate, the ester of glycerol and of palmitic and stearic acids, polyoxyethylene 2 OE monostearate, glyceryl mono- and dibehenate, pentaerythritol tetrastearate and their mixtures.

Preferably, the lipophilic surfactant is chosen from mono-, di- or triesters of sucrose and of fatty acids comprising from 12 to 30 carbon atoms, preferably from 14 to 20 carbon atoms, such as stearic acid, in particular sucrose tristearate, sucrose distearate and their mixtures.

The lipophilic surface-active agent can be present for example in a content ranging from 0.1 to 15% by weight, with respect to the total weight of the composition, preferably from 0.5 to 5% by weight. As noted above, the invention compositions can contain more than one lipophilic surface-active agent.

Hydrophilic Surfactant

The hydrophilic surface-active agent exhibits an HLB ranging from 8 to 12.

The hydrophilic surfactants with an HLB ranging from 8 to 12 can be chosen from:
- ethers of polyethylene glycol and/or of polypropylene glycol and of fatty alcohols, in particular of alcohols comprising from 12 to 30 carbon atoms, preferably from 14 to 22 carbon atoms, such as tridecyl alcohol, cetyl alcohol, stearyl alcohol or lauryl alcohol, the ether comprising in total from 2 to 30 oxyethylene (OE) and/or oxypropylene (OP) groups, preferably from 1 to 20 oxyethylene groups and/or from 1 to 10 oxypropylene groups, such as, for example, the compounds having the INCI names steareth-8, steareth-10, steareth-16, steareth-20, ceteth-10, laureth-4, laureth-3 (such as Remcopal 121 from Ceca S.A.), trideceth-6 (such as Renex 36 from ICI Surfactants), ceteareth-5 (such as Volpo CS 5 from Croda), oleth-10 (such as Volpo N 10 from Croda), beneth-10 (such as Nikkol BB-10 from Nikkol), the ether of oleyl alcohol and of polyethylene glycol comprising 4.5 OE groups (such as, for example, Remcopal 220 from Ceca S.A.), the polyoxy-propylenated (40P)/polyoxyethylenated (1 OE) ether of cetyl alcohol (such as Nikkol PBC-31 from Nikkol) or the polyoxypropylenated (40P)/polyoxyethylenated (10 OE) ether of cetyl alcohol (such as Nikkol PBC-33 from Nikkol), esters of polyethylene glycol and/or of polypropylene glycol and of fatty acids, in particular of fatty acids comprising from 12 to 30 carbon atoms, preferably from 14 to 26 carbon atoms, such as oleic acid or stearic acid, comprising from 1 to 50 oxyethylene (OE) groups, preferably from 4 to 12 oxyethylene groups, such as, for example, polyethylene glycol-8 monostearate (or polyoxyethylenated 8 OE monostearate), polyethylene glycol-10 monostearate (or polyoxyethylenated 10 OE monostearate), or polyethylene glycol-12 distearate (or polyoxyethylenated 12 OE distearate), ethers resulting from the reaction of a) polyethylene glycol and of b) esters of fatty acids (in particular of $C_{12}$-$C_{30}$ and preferably $C_{12}$-$C_{26}$ acids) and of glucose which are oxyethylenated (which can comprise from 1 to 50 oxyethylene groups, preferably from 4 to 10 oxyethylene groups, and from 1 to 10 glycosyl groups), such as ethers of polyethylene glycol and of esters of stearic acid and of glucose, such as polyoxyethylenated (20 OE) methyl glucose distearate, ethers of alcohols comprising from 12 to 30 carbon atoms, preferably from 14 to 22 carbon atoms, and of glycerol or of polyglycerol, the ethers comprising from 3 to 10 glycerol groups, such as, for example, polyglyceryl-3 cetyl ether, such as Chimexane NL from Chimex, esters of fatty acids comprising from 12 to 30 carbon atoms, better still from 14 to 20 carbon atoms, such as stearic acid, and of glycerol or of polyglycerol, the esters comprising from 3 to 10 glycerol groups, such as, for example, hexaglyceryl monostearate, it being possible for these glycerol or polyglycerol esters to comprise from 1 to 10 fatty chains;

esters of sucrose or of glucose and of fatty acids comprising from 12 to 30 carbon atoms, in particular from 14 to 20 carbon atoms; mention may be made, for example, of the mixture of esters (mono- and polyesters) of stearic acid and of sucrose sold by Croda under the reference Crodesta F110, ethers of fatty alcohols comprising from 12 to 30 carbon atoms, in particular from 12 to 20 carbon atoms, and of sucrose or of glucose, in particular ethers of fatty alcohols comprising from 12 to 20 carbon atoms and of glucose, comprising in particular from 1.2 to 3 glucoside units, such as the compounds carrying the INCI names C12-18 alkylglucoside, C12-20 alkylglucoside (for example Montanov L from Seppic), cetearyl glucoside (such as, for example, that which is sold as a mixture with cetearyl alcohol under the reference Montanov 68 from Seppic), myristyl glucoside (such as, for example, that which is sold as a mixture with myristyl alcohol under the reference Montanov 14 from Seppic) or cetearyl glucoside (such as Tegocare CG 90 from Evonik Goldschmidt), esters of sorbitol and/or of sorbitan and of fatty acids comprising from 12 to 30 carbon atoms, preferably from 12 to 20 carbon atoms, such as lauric acid; mention may be made, for example, of sorbitan laurate, such as Span 20 from Uniqema, ethers of sorbitol and/or of sorbitan, such as ethers of beeswax and of ethoxylated sorbitan comprising from 5 to 25 OE groups, such as, for example, Sorbeth-8 beeswax or Sorbeth-20 beeswax from GBW-125 Nikko Chemical, esters of fatty acids (in particular of $C_{12}$-$C_{30}$ and preferably $C_{12}$-$C_{20}$ acids) and of oxyethylenated ethers of sorbitol and/or of sorbitan (which can comprise from 2 to 30 oxyethylene groups), such as esters of stearic acid and of sorbitol and/or of sorbitan comprising from 2 to 20 OE groups, such as polysorbate-60, polysorbate-61, sorbeth-3 isostearate, polyoxyethylenated 4 OE sorbitan monostearate or polyoxyethylenated 20 OE sorbitan tristearate, ethers of polyethylene glycol and of cholesterol comprising from 5 to 40 oxyethylene groups, such as, for example, choleth-10 (such as Emalex CS-10 from Nihon Emulsion Company), choleth-15 (such as Emalex CS-15 from Nihon Emulsion Company) or choleth-20 (such as Emalex CS-20 from Nihon Emulsion Company), and their mixtures.

Preferably, the hydrophilic surfactant is chosen from:

ethers of polyethylene glycol and/or of polypropylene glycol and of fatty alcohols, in particular of alcohols comprising from 12 to 30 carbon atoms, preferably from 14 to 22 carbon atoms, such as tridecyl alcohol, cetyl alcohol, stearyl alcohol or lauryl alcohol, the ether comprising in total from 2 to 30 oxyethylene (OE) and/or oxypropylene (OP) groups, preferably from 1 to 20 oxyethylene groups and/or from 1 to 10 oxypropylene groups, such as, for example, the compounds having the INCI names steareth-10, ceteth-10, laureth-4, trideceth-6, esters of fatty acids (in particular of $C_{12}$-$C_{30}$ and preferably $C_{12}$-$C_{20}$ acids) and of oxyethylenated ethers of sorbitol and/or of sorbitan (which can comprise from 2 to 30 oxyethylene groups), such as esters of stearic acid and of sorbitol and/or of sorbitan comprising from 2 to 20 OE groups, such as polysorbate-60 (polyoxyethylenated 20 OE sorbitan monostearate), polysorbate-61 (polyoxyethylenated 4 OE sorbitan monostearate), sorbeth-3 isostearate, polyoxyethylenated 20 OE sorbitan tristearate, esters of fatty acids comprising from 12 to 30 carbon atoms, and of glycerol or of polyglycerol, the esters comprising from 3 to 10 glycerol groups, such as, for example, hexaglyceryl monostearate, and their mixtures.

Preferably, the hydrophilic surfactant is chosen from polyoxyethylenated 20 OE sorbitan monostearate, polyoxyethylenated 4 OE sorbitan monostearate, polyoxyethylenated 20 OE sorbitan tristearate, polyoxyethylenated (20 OE) methyl glucose distearate, polyoxyethylenated 8 OE monostearate, polyoxyethylenated 10 OE monostearate, polyoxyethylenated 12 OE distearate, hexaglyceryl monostearate, and their mixtures, and more preferably from polyoxyethylenated 20 OE sorbitan monostearate, polyoxyethylenated 4 OE sorbitan monostearate or a mixture.

The hydrophilic surface-active agent can preferably be present in a content ranging from 0.05 to 15% by weight, with respect to the total weight of the composition, more preferably from 0.1 to 10% by weight and more preferably from 0.5 to 5% by weight. As noted above, the invention compositions can contain more than one hydrophilic surface-active agent.

Amphiphilic Compound of Ionic Nature at a pH Ranging from 3 to 5.5

Amphiphilic compound of ionic nature at a pH ranging from 3 to 5.5 is understood to mean a compound comprising a lipophilic part and a hydrophilic part which is of ionic nature and the charge of which exists in this pH range in the normeutralized state. More specifically, this phrase is understood to mean a compound, at least 80% of the ionizable groups of which are in the form of ions at a pH ranging from 3 to 5.5.

Use is preferably made of amphiphilic compound of ionic nature at a pH ranging from 3 to 5, preferably from 4 to 5.

Such ionic amphiphilic compounds can be chosen from:
alkali metal salts of esters of phosphoric acid and of fatty alcohols comprising from 14 to 36 carbon atoms, preferably from 16 to 18 carbon atoms, such as cetyl alcohol or myristyl alcohol, in particular:
sodium and potassium salts of monocetyl phosphate, such as, for example, the compound sold under the reference Amphisol K by DSM,
alkali metal salts of dicetyl phosphate, in particular the sodium and potassium salts,
alkali metal salts of dimyristyl phosphate, in particular the sodium and potassium salts;
alkali metal salts of cholesterol sulphate, in particular the sodium salt; or alkali metal salts of cholesterol phosphate, in particular the sodium salt;
alkylsulphonic derivatives of formula:

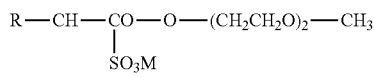

in which R represents the $C_{16}H_{33}$ and $C_{18}H_{37}$ radicals, taken as a mixture or separately, and M is an alkali metal, preferably sodium.

Preferably, the ionic amphiphilic compound is chosen from alkali metal salts of esters of phosphoric acid and of fatty alcohols comprising from 14 to 36 carbon atoms, preferably from 16 to 18 carbon atoms, such as cetyl alcohol or myristyl alcohol, in particular the sodium and potassium salts of monocetyl phosphate.

The ionic amphiphilic compound can be present in a content ranging from, for example, 0.05 to 10% by weight, with respect to the total weight of the composition, preferably from 0.5 to 5% by weight. More than one ionic amphiphilic compound can be present in the invention compositions.

The coating according to the invention of the oily globules preferably generally requires the use of a total amount of hydrophilic surface-active agent, of lipophilic surface-active agent and of ionic amphiphilic compound ranging from 2 to 6% by weight, preferably from 3 to 5% by weight, with respect to the total weight of the composition.

The relative amounts of lipophilic and hydrophilic surfactants and ionic amphiphilic compound preferably range respectively from 35 to 55% by weight, from 25 to 40% by weight and from 15 to 35% by weight, with respect to the total weight of the combined lipophilic and hydrophilic surfactants and ionic amphiphilic compound.

According to one embodiment, the composition according to the invention comprises:
at least one hydrophilic surfactant chosen from mono-, di- or triesters of sucrose and of fatty acids comprising from 12 to 30 carbon atoms, preferably from 14 to 20 carbon atoms, such as stearic acid, in particular sucrose tristearate, sucrose distearate and their mixtures,
at least one lipophilic surfactant chosen from esters of fatty acids (in particular $C_{12}$-$C_{30}$ and preferably $C_{12}$-$C_{20}$ acids) and of oxyethylenated ethers of sorbitol and/or of sorbitan (which can comprise from 2 to 30 oxyethylene groups), such as esters of stearic acid and of sorbitol and/or of sorbitan comprising from 2 to 20 OE groups, such as polysorbate 60, polysorbate 61, sorbeth-3 isostearate, polyoxyethylenated 4 OE sorbitan monostearate, polyoxyethylenated 20 OE sorbitan tristearate and their mixtures, and
at least one amphiphilic compound of ionic nature at a pH ranging from 3 to 5.5 chosen from alkali metal salts of esters of phosphoric acid and of fatty alcohols comprising from 14 to 36 carbon atoms, preferably from 16 to 18 carbon atoms, such as cetyl alcohol or myristyl alcohol, in particular the sodium and potassium salts of monocetyl phosphate.

According to one embodiment, the composition according to the invention is devoid of amphiphilic compounds of ionic nature at a pH of greater than 5.5, that is to say of compounds which, when they are dispersed in water without being neutralized, occur in the ionic form at this pH.

According to one embodiment, the composition according to the invention is devoid of fatty acids, in particular of stearic acid.

Aqueous Phase

The aqueous phase of the composition according to the invention comprises water and optionally one or more water-miscible or at least partially water-miscible compounds, such as polyols or lower $C_2$ to $C_8$ monoalcohols, such as ethanol and isopropanol. "Ambient temperature" should be understood as meaning a temperature of approximately 25° C., at standard atmospheric pressure (760 mmHg).

"Polyol" should be understood as meaning any organic molecule comprising at least two free hydroxyl groups. Mention may be made, as polyols, for example, of glycols, such as butylene glycol, propylene glycol, isoprene glycol, glycerol and polyethylene glycols, such as PEG-8, sorbitol or sugars, such as glucose.

The aqueous phase can also comprise any standard water-soluble or water-dispersible additive as indicated below.

The aqueous phase can represent from 60 to 98% by weight, preferably from 65 to 95% by weight, better still from 70 to 90% by weight and even better still from 70 to 85% by weight, with respect to the total weight of the composition.

This amount of aqueous phase does not comprise the amount of hydrophilic gelling agent or surfactant.

Gelling Agents

As set out above, the viscosity of the compositions of the invention can be adjusted using hydrophilic gelling agent(s) present in the continuous phase of the emulsion. Examples of hydrophilic gelling agents are:
modified or unmodified carboxyvinyl polymers, such as the products sold under the Carbopol (INCI name: carbomer) and Pemulen (INCI name: Acrylates/C10-30 alkyl acrylate crosspolymer) names by Goodrich;
polyacrylamides and polymers and copolymers of 2-acrylamido-2-methylpropanesulphonic acid which are optionally crosslinked and/or neutralized, such as the poly(2-acrylamido-2-methylpropanesulphonic acid) sold by Clariant under the name "Hostacerin AMPS" (INCI name: ammonium polyacryloyldimethyl taurate); or crosslinked anionic copolymers of acrylamide and of AMPS which are provided in the form of an emulsion, such as those sold under the name of Sepigel 305 (CTFA name: Polyacrylamide/C13-14 Isoparaffin/Laureth-7), under the name of Simulgel 600 (CTFA name: Acrylamide/Sodium Acryloyldimethyl Taurate Copolymer/Isohexadecane/Polysorbate 80) by SEPPIC or under the name of Simulgel EG (CTFA name: Sodium Acrylate/Sodium Acryloyldimethyl Taurate Copolymer and Isohexadecane and Polysorbate 80);

acrylate/acrylonitrile copolymers, such as Hypan SS201, sold by Kingston;

polysaccharide biopolymers, such as xanthan gum, guar gum, alginates or modified or unmodified celluloses;

inorganic compounds, such as smectites or modified or unmodified hectorites, such as the Bentone products sold by Rheox, the Laponite products sold by Southern Clay Products or the product Veegum HS sold by R. T. Vanderbilt;

and their mixtures.

Use is preferably made, as hydrophilic gelling agent, of optionally crosslinked polymers and copolymers of 2-acrylamido-2-methylpropanesulphonic acid.

The hydrophilic gelling agent can be present in the composition in a content (in dry material) ranging for example from 0.05% to 5% by weight, preferably from 0.1% to 3% by weight and better still from 0.3% to 2% by weight, with respect to the total weight of the composition.

According to a specific embodiment, the hydrophilic gelling agent is present in the composition in a content (in dry material) less than 2% by weight, with respect to the total weight of the composition, preferably less than 1% by weight.

This concentration is adjusted in order for the viscosity of the composition, measured using a Rheomat 180 viscometer at 25° C. for a rotational speed of 200 rpm, to advantageously be greater than or equal to 0.10 Pa·s.

Oily Phase

The oily phase is a fatty phase comprising at least one fatty substance chosen from fatty substances which are liquid at ambient temperature (20-25° C.) or oils, which may or may not be volatile, of vegetable, mineral or synthetic origin, and their mixtures. These oils are physiologically acceptable.

The oily phase can also comprise any standard fat-soluble or fat-dispersible additive as indicated below.

It can in particular comprise other fatty substances, such as waxes, pasty compounds, fatty alcohols or fatty acids. The oily phase comprises at least one oil, more particularly at least one cosmetic oil. "Oil" is understood to mean a fatty substance which is liquid at ambient temperature (25° C.).

Mention may be made, as oils which can be used in the composition of the invention, for example, of:

linear or branched hydrocarbons of mineral or synthetic origin, such as volatile or nonvolatile liquid paraffins and their derivatives, liquid petrolatum, polydecenes, isohexadecane, isododecane or hydrogenated polyisobutene, such as Parleam® oil;

volatile linear alkanes, advantageously of vegetable origin, comprising from 7 to 17 carbon atoms, in particular from 9 to 15 carbon atoms and more particularly from 11 to 13 carbon atoms.

Mention may be made, as examples of volatile linear alkanes suitable for the invention, of those described in the patent application of Cognis WO 2007/068371. Mention may be made, as examples of volatile linear alkanes suitable for the invention, of n-nonane ($C_9$), n-decane ($C_{10}$), n-undecane ($C_{11}$), n-dodecane ($C_{12}$), n-tri-decane ($C_{13}$), n-tetradecane ($C_{14}$), n-pentadecane ($C_{15}$), n-hexadecane ($C_{16}$) and n-heptadecane ($C_{17}$) and their mixtures. According to a particularly preferred form, use will be made of a mixture of undecane ($C_{11}$) and of tridecane ($C_{13}$), such as the product sold under the reference of Cetiol UT by Cognis;

hydrocarbon oils of vegetable origin, such as liquid triglycerides of fatty acids comprising from 4 to 10 carbon atoms, such as triglycerides of heptanoic acid or octanoic acid, or also, for example, sunflower, maize, soybean, pumpkin seed, grape seed, sesame, hazelnut, apricot, macadamia, arara, coriander, castor or avocado oils, triglycerides of caprylic/capric acids, such as those sold by Stéarineries Dubois or those sold under the names Miglyol 810, 812 and 818 by Dynamit Nobel, jojoba oil or shea butter oil;

synthetic esters and ethers, in particular of fatty acids, such as oils of formulae $R^1COOR^2$ and $R^1OR^2$ in which $R^1$ represents the residue of a fatty acid or of a fatty alcohol comprising from 8 to 29 carbon atoms and $R^2$ represents a branched or unbranched hydrocarbon chain comprising from 3 to 30 carbon atoms, such as, for example, purcellin oil, 2-octyldodecyl stearate, 2-octyldodecyl erucate or isostearyl isostearate; hydroxylated esters, such as isostearyl lactate, octyl hydroxystearate, octyldodecyl hydroxystearate, diisostearyl malate, triisocetyl citrate or heptanoates, octanoates or decanoates of fatty alcohols; polyol esters, such as propylene glycol dioctanoate, neopentyl glycol diheptanoate and diethylene glycol diisononanoate; and pentaerythritol esters, such as pentaerythrityl tetraisostearate; or lipophilic derivatives of amino acids, such as isopropyl lauroyl sarcosinate (INCI name), sold under the name Eldew SL 205 by Ajinomoto;

fluorinated oils which partially comprise hydrocarbon and/or silicone, such as those described in the document JP-A-2-295912;

silicone oils, such as volatile or non-volatile polymethylsiloxanes (PDMSs) comprising a linear or cyclic silicone chain which are liquid or pasty at ambient temperature, in particular volatile silicone oils, especially cyclopolydimethylsiloxanes (cyclomethicones), such as cyclohexadimethylsiloxane and cyclopentadimethylsiloxane; polydimethylsiloxanes comprising pendant alkyl, alkoxy or phenyl groups or alkyl, alkoxy or phenyl groups at the end of the silicone chain, which groups have from 2 to 24 carbon atoms; or phenylated silicones, such as phenyl trimethicones, phenyl dimethicones, phenyl(trimethylsiloxy)diphenylsiloxanes, diphenyl dimethicones, diphenyl(methyldiphenyl)trisiloxanes, (2-phenylethyl)trimethylsiloxysilicates and polymethylphenylsiloxanes;

their mixtures.

According to an embodiment, the composition of the invention comprises at least one oil chosen from silicone oils, linear or branched hydrocarbons, synthetic ethers and esters, and their mixtures, in particular chosen from volatile silicone oils and branched hydrocarbons, such as Parleam® oil, and their mixtures.

The amount of oily phase in the composition of the invention can range for example from 2 to 50% by weight, with respect to the total weight of the composition, from 5 to 30% by weight and better still from 7 to 25% by weight, with respect to the total weight of the composition.

This amount of oily phase does not comprise the amount of surfactant.

In particular, the composition according to the invention comprises from 2 to 50% by weight of oils, with respect to the total weight of the composition, preferably from 5 to 30% by weight of oils and better still from 7 to 25% by weight, with respect to the total weight of the composition.

According to a specific embodiment, the oily phase of the composition according to the invention comprises at least one ester oil chosen from lipophilic derivatives of amino acids, such as isopropyl lauroyl sarcosinate, esters of linear or branched fatty acids comprising from 8 to 29 carbon atoms and of linear or branched alcohols, preferably branched alcohols, comprising from 3 to 15 carbon atoms, such as isopropyl myristate or isononyl isononanoate, and their mixtures. Such oils allow to improve the stability of the composition.

According to a specific embodiment, the oily phase of the composition according to the invention comprises at least 25% by weight, relative to the total weight of the oily phase, of at least one ester oil chosen from lipophilic derivatives of amino acids, such as isopropyl lauroyl sarcosinate, esters of linear or branched fatty acids comprising from 8 to 29 carbon atoms and of linear or branched alcohols, preferably branched alcohols, comprising from 3 to 15 carbon atoms, such as isopropyl myristate or isononyl. More specifically, in one embodiment the above mentioned ester oils represent at least 25% by weight relative to the total weight of the oils of the composition.

Additives

The composition of the invention can also comprise one or more adjuvants including those known and normal in the cosmetic or dermatological field. Mention may be made, as adjuvants, for example, of active principles, preservatives, antioxidants, fragrances, solvents, salts, fillers, sunscreens (=UV screening agents), colouring materials, and also lipid vesicles or any other type of vector (microcapsules, for example), and their mixtures. These adjuvants may be used in the proportions usual in the cosmetic field, for example from 0.01 to 30% of the total weight of the composition, and they are, depending on their nature, introduced into the aqueous phase of the composition or into the oily phase, or also into vesicles or any other type of vector. These adjuvants and their concentrations should be such that they do not modify the property desired for the emulsion of the invention, in particular the pH of the composition.

Mention may be made, as fillers which can be used in the composition of the invention, for example, of pigments, such as titanium, zinc or iron oxides and organic pigments; kaolin; silica; talc; boron nitride; spherical organic powders; fibres; and their mixtures. Mention may be made, as spherical organic powders, for example, of polyamide powders and in particular Nylon®, such as Nylon-1 or Polyamide 12, powders sold under the Orgasol names by Atochem; polyethylene powders; Teflon®; microspheres based on acrylic copolymers, such as those made of ethylene glycol dimethacrylate/lauryl methacrylate copolymer sold by Dow Corning under the name Polytrap; expanded powders, such as hollow microspheres and in particular the microspheres sold under the name Expancel by Kemanord Plast or under the name Micropearl F 80 ED by Matsumoto; silicone resin microbeads, such as those sold under the name Tospearl by Toshiba Silicone; polymethyl methacrylate microspheres, sold under the name Microsphere M-100 by Matsumoto or under the name Covabead LH85 by Wackherr; ethylene/acrylate copolymer powders, such as those sold under the name Flobeads by Sumitomo Seika Chemicals; or powders formed from natural organic materials, such as starch powders, in particular powders formed from crosslinked or noncrosslinked maize, wheat or rice starches, such as the powders formed from starch crosslinked with octenyl succinic anhydride sold under the name Dry-Flo by National Starch. Mention may be made, as fibres, for example, of polyamide fibres, such as in particular fibres formed from Nylon 6 (or Polyamide 6) (INCI name: Nylon 6) or from Nylon 6,6 (or Polyamide 66) (INCI name: Nylon 66) or such as fibres formed from poly(p-phenylene terephthalamide); and their mixtures. These fillers can be present in amounts ranging from 0 to 20% by weight and preferably from 0.5 to 10% by weight, with respect to the total weight of the composition.

Mention may be made, as active principles which can be used in the composition of the invention, for example, of moisturizing agents, such as protein hydrolysates; sodium hyaluronate; polyols, such as glycerol, glycols, such as polyethylene glycols, and sugar derivatives; antiinflammatories; procyanidol oligomers; vitamins, such as vitamin A (retinol), vitamin E (tocopherol), vitamin K, vitamin C (ascorbic acid), vitamin B5 (panthenol), vitamin B3 or PP (niacinamide), the derivatives of these vitamins (in particular esters) and their mixtures; keratolytic and/or desquamating agents, such as salicylic acid and its derivatives, α-hydroxy acids, such as lactic acid and glycolic acid, and their derivatives, and ascorbic acid and its derivatives; urea; caffeine; depigmenting agents, such as kojic acid, hydroquinone and caffeic acid; salicylic acid and its derivatives; retinoids, such as carotenoids and vitamin A derivatives; hydrocortisone; melatonin; algal, fungal, plant, yeast or bacterial extracts; steroids; antibacterial active principles, such as 2,4,4'-trichloro-2'-hydroxydiphenyl ether (or triclosan), 3,4,4'-trichlorocarbanilide (or triclocarban) and the acids indicated above and in particular salicylic acid and its derivatives; enzymes; flavonoids; tightening agents, such as synthetic polymers, plant proteins, polysaccharides of plant origin in or not in the form of microgels, starches, wax dispersions, mixed silicates and colloidal particles of inorganic fillers; ceramides; antiinflammatory agents; soothing agents; mattifying agents; agents for combating hair loss and/or for regrowth of the hair; antiwrinkle agents; essential oils; and their mixtures; and any active principle appropriate for the final objective of the composition.

The UV screening agents can be organic or inorganic (or physical UV screening agents). They can be present in an amount as active material ranging from 0.01 to 20% by weight of active material, preferably from 0.1 to 15% by weight and better still from 0.2 to 10% by weight, with respect to the total weight of the composition.

Mention may be made, as examples of organic screening agents or photoprotective agents, of those denoted below under their INCI names:

Dibenzoylmethane Derivatives:
Butylmethoxydibenzoylmethane, sold in particular under the trade name "Parsol MCX" by DSM Nutritional Products Inc.,
Cinnamic Derivatives:
Ethylhexyl Methoxycinnamate, sold in particular under the trade name "Parsol MCX" by DSM Nutritional Products Inc.,
Isopropyl Methoxycinnamate,
Isoamyl Methoxycinnamate, sold under the trade name "Neo Heliopan E 1000" by Symrise,
DEA Methoxycinnamate,
Diisopropyl Methylcinnamate,
Glyceryl Ethylhexanoate Dimethoxycinnamate,
para-Aminobenzoic Acid Derivatives:
PABA,
Ethyl PABA,
Ethyl Dihydroxypropyl PABA,
Ethylhexyl Dimethyl PABA, sold in particular under the name "Escalol 507" by ISP,
Glyceryl PABA,
PEG-25 PABA, sold under the name "Uvinul P25" by BASF, Salicylic Derivatives:
Homosalate, sold under the name "Eusolex HMS" by Rona/EM Industries,
Ethylhexyl Salicylate, sold under the name "Neo Heliopan OS" by Symrise,
Dipropyleneglycol Salicylate, sold under the name "Dipsal" by Scher,
TEA Salicylate, sold under the name "Neo Heliopan TS" by Symrise,
β,β-Diphenylacrylate Derivatives:
Octocrylene, sold in particular under the trade name "Uvinul N539" by BASF,
Etocrylene, sold in particular under the trade name "Uvinul N35" by BASF,
Benzophenone Derivatives:
Benzophenone-1, sold under the trade name "Uvinul 400" by BASF,
Benzophenone-2, sold under the trade name "Uvinul D50" by BASF,
Benzophenone-3 or Oxybenzone, sold under the trade name "Uvinul M40" by BASF,
Benzophenone-4, sold under the trade name "Uvinul MS40" by BASF,
Benzophenone-5,
Benzophenone-6, sold under the trade name "Helisorb 11" by Norquay,
Benzophenone-8, sold under the trade name "SpectraSorb UV-24" by American Cyanamid,
Benzophenone-9, sold under the trade name "Uvinul DS-49" by BASF,
Benzophenone-12,
n-Hexyl 2-(4-diethylamino-2-hydroxybenzoyl)benzoate, sold under the trade name "Uvinul A+" by BASF,
Benzylidenecamphor Derivatives:
3-Benzylidene camphor, manufactured under the name "Mexoryl SD" by Chimex,
4-Methylbenzylidene camphor, sold under the name "Eusolex 6300" by Merck,
Benzylidene Camphor Sulfonic Acid, manufactured under the name "Mexoryl SL" by Chimex,
Camphor Benzalkonium Methosulfate, manufactured under the name "Mexoryl SO" by Chimex,
Terephthalylidene Dicamphor Sulfonic Acid, manufactured under the name "Mexoryl SX" by Chimex,
Polyacrylamidomethyl Benzylidene Camphor, manufactured under the name "Mexoryl SW" by Chimex,
Phenylbenzimidazole Derivatives:
Phenylbenzimidazole Sulfonic Acid, sold in particular under the trade name "Eusolex 232" by Merck,
Disodium Phenyl Dibenzimidazole Tetrasulfonate, sold under the trade name "Neo Heliopan AP" by Symrise,
Phenylbenzotriazole Derivatives:
Drometrizole Trisiloxane, sold under the name "Silatrizole" by Rhodia Chimie,
Methylene Bis-Benzotriazolyl Tetramethylbutylphenol, sold in the solid form under the trade name "Mixxim BB/100" by Fairmount Chemical or in the micronized form in aqueous dispersion under the trade name "Tinosorb M" by Ciba Specialty Chemicals,
Triazine Derivatives:
Bis-Ethylhexyloxyphenol Methoxyphenyl Triazine, sold under the trade name "Tinosorb S" by Ciba-Geigy,
Ethylhexyl Triazone, sold in particular under the trade name "Uvinul T150" by BASF,
Diethylhexyl Butamido Triazone, sold under the trade name "Uvasorb HEB" by Sigma 3V,
2,4,6-Tris(dineopentyl 4'-aminobenzalmalonate)-s-triazine,
2,4,6-Tris(diisobutyl 4'-aminobenzalmalonate)-s-triazine,
2,4-Bis(n-butyl 4'-aminobenzoate)-6-(aminopropyltrisiloxane)-s-triazine,
2,4-Bis(dineopentyl 4'-aminobenzalmalonate)-6-(n-butyl 4'-aminobenzoate)-s-triazine,
The symmetrical triazine screening agents described in U.S. Pat. No. 6,225,467, Application WO 2004/085412 (see compounds 6 and 9) or the document "Symmetrical Triazine Derivatives", IP.COM Journal, IP.COM INC, WEST HENRIETTA, NY, US (20 Sep. 2004), in particular the 2,4,6-tris(biphenyl)-1,3,5-triazines (especially 2,4,6-tris(biphenyl-4-yl)-1,3,5-triazine) and 2,4,6-tris(terphenyl)-1,3,5-triazine, which is taken up again in Patent Applications WO 06/035000, WO 06/034982, WO 06/034991, WO 06/035007, WO 2006/034992 and WO 2006/034985.
Anthranilic Derivatives:
Menthyl anthranilate, sold under the trade name "Neo Heliopan MA" by Symrise,
Imidazoline Derivatives:
Ethylhexyl Dimethoxybenzylidene Dioxoimidazoline Propionate,
Benzalmalonate Derivatives:
Polyorganosiloxane comprising benzalmalonate functional groups, such as Polysilicone-15, sold under the trade name "Parsol SLX" by DSM Nutritional Products Inc.,
4,4-Diarylbutadiene Derivatives:
1,1-Dicarboxy(2,2'-dimethylpropyl)-4,4-diphenylbutadiene,
Benzoxazole Derivatives:
2,4-Bis[5-1-(dimethylpropyl)benzoxazol-2-yl-(4-phenyl)imino]-6-(2-ethylhexyl)imino-1,3,5-triazine, sold under the name of Uvasorb K2A by Sigma 3V,
Merocyanine Derivatives:
Octyl 5-(N,N-diethylamino)-2-phenylsulfonyl-2,4-pentadienoate,
and their mixtures.
The preferred organic screening agents are chosen from:
Butylmethoxydibenzoylmethane,
Ethylhexyl Methoxycinnamate,
Ethylhexyl Salicylate,
Homosalate,
Octocrylene,
Phenylbenzimidazole Sulfonic Acid,
Benzophenone-3,
n-Hexyl 2-(4-diethylamino-2-hydroxybenzoyl)benzoate,
Terephthalylidene Dicamphor Sulfonic Acid,
Methylene Bis-Benzotriazolyl Tetramethylbutylphenol,
Bis-Ethylhexyloxyphenol Methoxyphenyl Triazine,
Ethylhexyl triazone,
Diethylhexyl Butamido Triazone,
2,4,6-Tris(dineopentyl 4'-aminobenzalmalonate)-s-triazine,
2,4,6-Tris(diisobutyl 4'-aminobenzalmalonate)-s-triazine,
2,4-Bis(n-butyl 4'-aminobenzoate)-6-(aminopropyltrisiloxane)-s-triazine,
2,4-Bis(dineopentyl 4'-aminobenzalmalonate)-6-(n-butyl 4'-aminobenzoate)-s-triazine,
Drometrizole Trisiloxane,
Octyl 5-(N,N-diethylamino)-2-phenylsulfonyl-2,4-pentadienoate,
and their mixtures.
The inorganic screening agents can be chosen from pigments formed of metal oxides which may or may not be coated, the mean size of the primary particles of which is preferably between $5\times10^{-3}$ µm and $100\times10^{-3}$ µm (preferably between $10\times10^{-3}$ µm and $50\times10^{-3}$ µm), such as, for example, pigments formed of titanium oxide (amorphous or crystalline in the rutile and/or anatase form), iron oxide, zinc oxide, zirconium oxide or cerium oxide, or their mixtures, which are all UV photoprotective agents well known per se.

The pigments may or may not be coated.

The coated pigments are pigments which have been subjected to one or more surface treatments of chemical, electronic, mechanochemical and/or mechanical nature with compounds such as described, for example, in Cosmetics & Toiletries, February 1990, Vol. 105, pp. 53-64, such as amino acids, beeswax, fatty acids, fatty alcohols, anionic surfactants, lecithins, sodium, potassium, zinc, iron or aluminium salts of fatty acids, metal alkoxides (titanium or aluminium alkoxides), polyethylene, silicones, proteins (collagen, elastin), alkanolamines, silicon oxides, metal oxides or sodium hexametaphosphate.

The coated pigments are more particularly titanium oxides coated:
- with silica, such as the product "Sunveil" from Ikeda and the product "Eusolex T-AVO" from Merck,
- with silica and with iron oxide, such as the product "Sunveil F" from Ikeda,
- with silica and with alumina, such as the products "Microtitanium Dioxide MT 500 SA" and "Microtitanium Dioxide MT 100 SA" from Tayca, "Tioveil" from Tioxide and "Mirasun TiW 60" from Rhodia,
- with alumina, such as the products "Tipaque TTO-55 (B)" and "Tipaque TTO-55 (A)" from Ishihara and "UVT 14/4" from Kemira,
- with alumina and with aluminium stearate, such as the product "Microtitanium Dioxide MT 100 TV, MT 100 TX, MT 100 Z or MT-01 from Tayca and the products "Solaveil CT-10 W", "Solaveil CT 100" and "Solaveil CT 200" from Uniqema,
- with silica, with alumina and with alginic acid, such as the product "MT-100 AQ" from Tayca,
- with alumina and with aluminium laurate, such as the product "Microtitanium Dioxide MT 100 S" from Tayca,
- with iron oxide and with iron stearate, such as the product "Microtitanium Dioxide MT 100 F" from Tayca,
- with zinc oxide and with zinc stearate, such as the product "BR351" from Tayca,
- with silica and with alumina and treated with a silicone, such as the products "Microtitanium Dioxide MT 600 SAS", "Microtitanium Dioxide MT 500 SAS" or "Microtitanium Dioxide MT 100 SAS" from Tayca,
- with silica, with alumina and with aluminium stearate and treated with a silicone, such as the product "STT-30-DS" from Titan Kogyo,
- with silica and treated with a silicone, such as the product "UV-Titan X 195" from Kemira or the product SMT-100 WRS from Tayca,
- with alumina and treated with a silicone, such as the products "Tipaque TTO-55 (S)" from Ishihara or "UV Titan M 262" from Kemira,
- with triethanolamine, such as the product "STT-65-S" from Titan Kogyo,
- with stearic acid, such as the product "Tipaque TTO-55 (C)" from Ishihara,
- with sodium hexametaphosphate, such as the product "Microtitanium Dioxide MT 150 W" from Tayca.

Other titanium oxide pigments treated with a silicone are preferably $TiO_2$ treated with octyltrimethylsilane and for which the mean size of the individual particles is between $25\times10^{-3}$ and $40\times10^{-3}$ µm, such as that sold under the trade name "T 805" by Degussa Silices, $TiO_2$ treated with a polydimethylsiloxane and for which the mean size of the individual particles is $21\times10^{-3}$ µm, such as that sold under the trade name "70250 Cardre UF TiO2S13" by Cardre, anatase/rutile $TiO_2$ treated with a polydimethylhydrosiloxane and for which the mean size of the individual particles is $25\times10^{-3}$ µm, such as that sold under the trade name "Microtitanium Dioxyde USP Grade Hydrophobic" by Color Techniques.

The uncoated titanium oxide pigments are, for example, sold by Tayca under the trade names "Microtitanium Dioxide MT 500 B" or "Microtitanium Dioxide MT600 B", by Degussa under the name "P 25", by Wacker under the name "Oxyde de titane transparent PW", by Miyoshi Kasei under the name "UFTR", by Tomen under the name "ITS" and by Tioxide under the name "Tioveil AQ".

The coated zinc oxide pigments are, for example:
- those sold under the name "Z-cote HP1" by Sunsmart (ZnO coated with dimethicone);
- those sold under the name "Oxide zinc CS-5" by Toshibi (ZnO coated with polymethylhydrosiloxane);
- those sold under the name "Daitopersion Zn-30" and "Daitopersion Zn-50" by Daito (dispersions in oxyethylenated polydimethylsiloxane/cyclopolymethylsiloxane comprising 30% or 50% of zinc oxides coated with silica and polymethylhydrosiloxane);
- those sold under the name "NFD Ultrafine ZnO" by Daikin (ZnO coated with phosphate of perfluoroalkyl and copolymer based on perfluoroalkylethyl as a dispersion in cyclopentasiloxane);
- those sold under the name "SPD-Z1" by Shin-Etsu (ZnO coated with silicone-grafted acrylic polymer dispersed in cyclodimethylsiloxane);
- those sold under the name "Escalol 2100" by ISP (alumina-treated ZnO dispersed in the ethylhexyl methoxycinnamate/PVP-hexadecene copolymer/methicone mixture);
- those sold under the name "Fuji ZnO-SMS-10" by Fuji Pigment (ZnO coated with silica and polymethylsilsesquioxane).

The uncoated cerium oxide pigments are sold, for example, under the name "Colloidal Cerium Oxide" by Rhône-Poulenc.

Uncoated iron oxide pigments with a size of the order of $10^{-3}$ microns are, for example, sold by Arnaud or by Mitsubishi under the name "TY-220".

The coated iron oxide pigments are, for example, sold by Arnaud under the names or by BASF under the name "Oxyde de fer transparent".

Mention may also be made of mixtures of metal oxides, in particular of titanium dioxide and of cerium dioxide, including the mixture of equal weights of titanium dioxide coated with silica and of cerium dioxide coated with silica sold by Ikeda under the name "Sunveil A", and also the mixture of titanium dioxide and of zinc dioxide coated with alumina, with silica and with silicone, such as the product "M 261" sold by Kemira, or coated with alumina, with silica and with glycerol, such as the product "M 211" sold by Kemira.

The total amount of organic UV screening agents in the compositions according to the invention can range, for example, from 0.1 to 20% by weight, with respect to the total weight of the composition, and preferably from 0.2 to 10% by weight, with respect to the total weight of the composition.

Mention may be made, as physical screening agents which can be added to the composition of the invention, for example, of pigments formed of metal oxides which may or may not be coated, in particular titanium, iron, zirconium, zinc or cerium oxides, and their mixtures, it being possible for these oxides to be in the form of particles of micronic size or with a size of the order of $10^{-3}$ microns which are optionally coated.

The compositions are most frequently provided in the form of a spray, milk, cream or gel, other presentation modes not being excluded. They are transparent or translucent when the size of the particles is less than $80 \times 10^{-3}$ μm.

The compositions according to the invention can be prepared by a process employing a first stage in which the fatty phase, comprising the lipophilic surfactant, the hydrophilic surfactant, the ionic amphiphilic compound and the active principle, if present, is mixed with stirring and a second stage in which the aqueous phase is introduced into the oily phase and then the mixture obtained is kept stirred in a vessel provided with a turbine mixer.

The invention will now be more fully described, in its subject-matters and its characteristics, using the examples which will follow.

EXAMPLES

In the following examples, the size of the oil drops (or oily globules) and the viscosity are measured in accordance with the methods indicated above.

Example 1

Milk for the Body and Fluid for the Face

|  | Example 1 (invention) | Example 2 (invention) |
|---|---|---|
| Aqueous phase A |  |  |
| Glycerol | 5 g | 5 g |
| Preservative | 0.65 g | 0.65 g |
| Demineralized water | 24.95 g | 24.95 g |
| Oily phase B |  |  |
| Potassium monocetyl phosphate (Amphisol K from DSM) | 0.4 g | 0.4 g |
| Polysorbate 61 (Tween 61V from Croda) | 0.8 g | 0.8 g |
| Sucrose tristearate (Ryoto Sugar Ester S 370 from Mitsubishi) | 1.7 g | 1.7 g |
| Hydrogenated polyisobutene | 12.5 g | 12.5 g |
| Isopropyl lauroyl sarcosinate | 12.5 g | 12.5 g |
| Preservative | 0.1 g | 0.1 g |
| Aqueous phase C |  |  |
| Demineralized water | q.s. for 100 g | q.s. for 100 g |
| Ammonium polyacryloyldimethyl taurate (Hostacerin AMPS from Clariant) | 0.35 g | 0.40 g |
| Citric acid | 0.034 g | 0.034 g |
| Viscosity (Rheomat 180, 25° C., 200 rpm) | 0.175 Pa · s | 0.25 Pa · s |
| pH | 4.8 | 4.8 |
| Size of the drops at t0 | 0.560 μm | 0.560 μm |
| Stability after 2 months from 4° C. to 45° C. | Good | Good |

Method of Preparation

The aqueous phase is prepared by dissolving the preservative and the glycerol in the water at 75° C. The hydrogenated polyisobutene and the isopropyl lauroyl sarcosinate are mixed at 75° C. until a homogeneous solution is obtained. The surfactants are then introduced into this solution with stirring. The aqueous phase (70° C.) is then rapidly added to the oily phase with stirring using a mixer of Maxi Lab (Olsa) type at the speed of 4000 rpm (turbine mixer). The emulsification is maintained at 75° C. for 15 minutes at the same rotational speed and then the temperature is reduced to 25° C. over 20 minutes using a turbine mixer at the speed of 4000 rpm. An oil-in-water emulsion is obtained.

The ammonium polyacryloyldimethyl taurate gelling agent is swollen in a portion of the aqueous phase using a deflocculator of Rayneri type (500 rpm) and then introduced at the end of formulation at ambient temperature with stirring (Maxi Lab, turbine mixer at the speed of 2000 rpm). Stirring at the speed of 4000 rpm is then maintained for 30 minutes.

The emulsions of compositions 1 and 2 of the invention are milk and fluid which are stable after two months from 4° C. to 45° C.

Examples 3 to 5

Face Fluids

The following are prepared:

- an emulsion according to the invention comprising an amphiphilic compound of ionic nature at a pH from 3 to 5.5 (Example 3),
- an emulsion outside the invention (Example 4), comprising an amphiphilic compound which is not of ionic nature at a pH from 3 to 5.5, and an emulsion outside the invention (Example 5), comprising stearic acid.

|  | Example 3 (invention) | Example 4 (outside the invention) | Example 5 (outside the invention) |
|---|---|---|---|
| Aqueous phase A |  |  |  |
| Glycerol | 5 g | 5 g | 5 g |
| Preservative | 0.65 g | 0.65 g | 0.65 g |
| Demineralized water | 25.15 g | 25.15 g | 25.15 g |
| Oily phase B |  |  |  |
| Potassium monocetyl phosphate (Amphisol K by DSM) | 0.6 g | 0 g | 0 g |
| Sodium stearoyl glutamate | 0 g | 0.6 g | 0 g |
| Stearic acid | 0 g | 0 g | 0.6 g |
| Polysorbate 61 (Tween 61V from Croda) | 0.8 g | 0.8 g | 0.8 g |
| Sucrose tristearate (Ryoto Sugar Ester S 370 from Mitsubishi) | 1.7 g | 1.7 g | 1.7 g |
| Hydrogenated polyisobutene | 18.5 g | 18.5 g | 18.5 g |
| Isopropyl lauroyl sarcosinate | 6.5 g | 6.5 g | 6.5 g |
| Preservative | 0.1 g | 0.1 g | 0.1 g |

|  | Example 3 (invention) | Example 4 (outside the invention) | Example 5 (outside the invention) |
|---|---|---|---|
| Aqueous phase C | | | |
| Demineralized water | q.s. for 100 g | q.s. for 100 g | q.s. for 100 g |
| Ammonium polyacryloyldimethyl taurate (Hostacerin AMPS from Clariant) | 0.40 g | 0.40 g | 0.40 g |
| Citric acid | 0.034 g | 0.034 g | 0.034 g |
| Viscosity (Rheomat 180, 25° C., 200 rpm) | 0.18 Pa·s | 0.2 Pa·s | 0.15 Pa·s |
| pH | 5 | 5 | 5 |
| Size of the drops at t0 | 0.460 μm | 1 μm | 2 μm |
| Stability after 2 months from 4° C. to 45° C. | Good | Unstable | Unstable |

Method of Preparation

The aqueous phase is prepared by dissolving the preservative and the glycerol in the water at 75° C. The hydrogenated polyisobutene and the isopropyl lauroyl sarcosinate are mixed at 75° C. until a homogeneous solution is obtained. The surfactants are then introduced into this solution with stirring. The aqueous phase (70° C.) is then rapidly added to the oily phase with stirring using a mixer of Maxi Lab (Olsa) type at the speed of 4000 rpm (turbine mixer). The emulsification is maintained at 75° C. for 15 minutes at the same rotational speed and then the temperature is reduced to 25° C. over 20 minutes using a turbine mixer at the speed of 4000 rpm.

An oil-in-water emulsion is obtained.

The ammonium polyacryloyldimethyl taurate gelling agent is swollen in a portion of the aqueous phase using a deflocculator of Rayneri type (500 rpm) and then introduced at the end of formulation at ambient temperature with stirring (Maxi Lab, turbine mixer at the speed of 2000 rpm). Stirring at the speed of 4000 rpm is then maintained for 30 minutes.

Properties of the Emulsions

The emulsion of composition 3 of the invention is a fluid which is stable after two months from 4° C. to 45° C.

The emulsions of compositions 4 and 5 (outside the invention), comprising an amphiphilic compound which is nonionic in the range from 3 to 5.5 (sodium stearoyl glutamate or stearic acid), exhibit a phenomenon of creaming (rise of the oil globules to the surface of the composition) after one month at 25° C.

These examples show the importance of the nature of the ionic amphiphilic compound on the stability of the emulsions.

Example 6 According to the Invention

Care Cream for the Face

| Aqueous phase A | |
|---|---|
| Glycerol | 5 g |
| Preservative | 0.65 g |
| Demineralized water | 25.15 g |
| Oily phase B | |
| Potassium monocetyl phosphate (Amphisol K from DSM) | 0.6 g |
| Polysorbate 61 (Tween 61V from Croda) | 0.8 g |
| Sucrose tristearate (Ryoto Sugar Ester S 370 from Mitsubishi) | 1.7 g |
| Hydrogenated polyisobutene | 18.75 g |
| Isopropyl myristate | 3.12 g |
| Isononyl isononanoate | 3.12 g |
| Preservative | 0.1 g |
| Aqueous phase C | |
| Demineralized water | q.s. for 100 g |
| Ammonium polyacryloyldimethyl taurate (Hostacerin AMPS from Clariant) | 1.5 g |
| Citric acid | 0.034 g |
| Viscosity (Rheomat 180, 25° C., 200 rpm) | 1.2 Pa·s |
| pH | 4.8 |
| Size of the drops at t0 | 0.672 μm |
| Stability after 2 months from 4° C. to 45° C. | Good |

Method of Preparation

The aqueous phase is prepared by dissolving the preservative and the glycerol in the water at 75° C. The hydrogenated polyisobutene, the isopropyl myristate and the isononyl isononanoate are mixed at 75° C. until a homogeneous solution is obtained. The surfactants are then introduced into this solution with stirring. The aqueous phase (70° C.) is then rapidly added to the oily phase with stirring using a mixer of Maxi Lab (Olsa) type at the speed of 4000 rpm (turbine mixer). The emulsification is maintained at 75° C. for 15 minutes at the same rotational speed and then the temperature is reduced to 25° C. over 20 minutes using a turbine mixer at the speed of 4000 rpm.

An oil-in-water emulsion is obtained.

The ammonium polyacryloyldimethyl taurate gelling agent is swollen in a portion of the aqueous phase using a deflocculator of Rayneri type (500 rpm) and then introduced at the end of formulation at ambient temperature with stirring (Maxi Lab, turbine mixer at the speed of 2000 rpm). Stirring at the speed of 4000 rpm is then maintained for 30 minutes.

Properties of the Emulsions

The emulsion of composition 6 of the invention is a cream which is stable after two months from 4° C. to 45° C.

The above written description of the invention provides a manner and process of making and using it such that any person skilled in this art is enabled to make and use the same, this enablement being provided in particular for the subject matter of the appended claims, which make up a part of the original description.

As used herein, the words "a" and "an" and the like carry the meaning of "one or more."

The phrases "selected from the group consisting of," "chosen from," and the like include mixtures of the specified materials. Terms such as "contain(s)" and the like are open terms meaning 'including at least' unless otherwise specifically noted.

All references, patents, applications, tests, standards, documents, publications, brochures, texts, articles, etc. mentioned herein are incorporated herein by reference. Where a numerical limit or range is stated, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein. In this regard, certain embodiments within the invention may not show every benefit of the invention, considered broadly.

The invention claimed is:

1. A composition in the form of an oil-in-water emulsion comprising:
    an aqueous phase comprising a hydrophilic gelling agent; and
    an oily phase of oily globules having a lamellar liquid crystal coating, the lamellar liquid crystal coating, consisting of:
    a monolamellar layer and an oligolamellar layer of at least one lipophilic surface-active agent which is an ester with an HLB of 2 to 5; at least one hydrophilic surface-active agent which is an ester with an HLB of 8 to 12; and an alkali metal salt of monocetyl phosphate;
    wherein
    the pH of the composition is from 3 to 4.8.

2. The composition according to claim 1, wherein the at least one lipophilic surface-active agent is selected from the group consisting of:
    esters of polyethylene glycol and of fatty acids,
    esters of polyethylene glycol and of fatty acids which are glycosylated,
    esters of fatty acids comprising from 12 to 30 carbon atoms and of glycerol or of polyglycerol, the esters comprising from 1 to 10 glycerol groups,
    esters of sucrose and of fatty acids comprising from 12 to 30 carbon atoms,
    esters of pentaerythritol and of fatty acids comprising from 12 to 30 carbon atoms, and
    esters of sorbitol and/or of sorbitan and of fatty acids comprising from 12 to 30 carbon atoms.

3. The composition according to claim 1, wherein the at least one lipophilic surface-active agent is selected from the group consisting of sucrose distearate, sucrose tristearate, diglyceryl distearate, tetraglyceryl tristearate, decaglyceryl decastearate, diglyceryl monostearate, hexaglyceryl tristearate, decaglyceryl pentastearate, sorbitan monostearate, sorbitan tristearate, diethylene glycol monostearate, the ester of glycerol and of palmitic and stearic acids, polyoxyethylene 2 OE monostearate, glyceryl mono- and dibehenate, and pentaerythritol tetrastearate.

4. The composition according to claim 1, wherein the hydrophilic surface-active agent is selected from the group consisting of mono-, di- or triesters of sucrose and of fatty acids comprising from 12 to 30 carbon atoms.

5. The composition according to claim 1, wherein the content of the at least one lipophilic surface-active agent is from 0.1 to 15% by weight with respect to the total weight of the composition.

6. The composition according to claim 1, wherein the at least one hydrophilic surface-active agent is selected from the group consisting of:
    esters of polyethylene glycol and/or of polypropylene glycol and of fatty acids, the esters comprising from 1 to 50 oxyethylene (OE) groups,
    esters of fatty acids comprising from 12 to 30 carbon atoms and of glycerol or of polyglycerol, the esters comprising from 3 to 10 glycerol groups,
    esters of sucrose or of glucose and of fatty acids comprising from 12 to 30 carbon atoms,
    esters of sorbitol and/or of sorbitan and of fatty acids comprising from 12 to 30 carbon atoms, and
    esters of fatty acids and of oxyethylenated ethers of sorbitol and/or of sorbitan having from 2 to 30 oxyethylene groups.

7. The composition according to claim 1, wherein the content of the at least one hydrophilic surface-active agent is from 0.05 to 15% by weight with respect to the total weight of the composition.

8. The composition according to claim 1, wherein the at least one hydrophilic surface-active agent is selected from the group consisting of polyoxyethylenated 4 OE sorbitan monostearate, polyoxyethylenated 20 OE sorbitan monostearate, polyoxyethylenated 20 OE sorbitan tristearate, polyoxyethylenated 8 OE monostearate, hexaglyceryl monostearate, polyoxyethylenated 10 OE monostearate, polyoxyethylenated 12 OE distearate and polyoxyethylenated 20 OE methyl glucose distearate.

9. The composition according to claim 1, wherein the alkali metal of the alkali metal salt of monocetyl phosphate is at least one of sodium and potassium.

10. The composition according to claim 1, wherein the content of the alkali metal salt of monocetyl phosphate is from 0.05 to 10% by weight with respect to the total weight of the composition.

11. The composition according to claim 1, comprising:
    from 35 to 55% by weight of the at least one lipophilic surfactant;
    from 25 to 40% by weight of the at least one hydrophilic surface-active agent; and
    from 15 to 35% by weight of the alkali metal salt of monocetyl phosphate; with respect to the total weight of the combined lipophilic and hydrophilic surfactants and alkali metal salt of monocetyl phosphate.

12. The composition according to claim 1, wherein the oily phase comprises an ester oil selected from the group consisting of lipophilic derivatives of amino acids, esters of linear or branched fatty acids comprising from 8 to 29 carbon atoms and of linear or branched alcohols comprising from 3 to 15 carbon atoms, and mixtures thereof.

13. The composition according to claim 12, wherein the content of the ester oil in the oily phase is at least 25% by weight with respect to the total weight of the composition.

14. The composition according to claim 1, wherein the viscosity of the composition is from 0.1 Pa·s to 100 Pa·s at a temperature of 25° C.

15. The composition according to claim 1, wherein the alkali metal salt of monocetyl phosphate is the sodium salt of monocetyl phosphate.

16. The composition according to claim 1, wherein the alkali metal salt of monocetyl phosphate is the potassium salt of monocetyl phosphate.

17. The composition according to claim 1, wherein the at least one hydrophilic surface-active agent is an ester of (1) a C12-C30 fatty acid and (2) sorbitol and/or of sorbitan, further comprising from 2 to 30 oxyethylenated groups.

18. The composition according to claim 2, wherein the at least one hydrophilic surface-active agent is an ester of (1) a C12-C30 fatty acid and (2) sorbitol and/or of sorbitan, further comprising from 2 to 30 oxyethylenated groups.

19. The composition according to claim 3, wherein the at least one hydrophilic surface-active agent is an ester of (1) a C12-C30 fatty acid and (2) sorbitol and/or of sorbitan, further comprising from 2 to 30 oxyethylenated groups.

20. The composition according to claim 6, wherein the at least one hydrophilic surface-active agent is an ester of (1) a C12-C30 fatty acid and (2) sorbitol and/or of sorbitan, further comprising from 2 to 30 oxyethylenated groups.

21. The composition according to claim 1, wherein the composition further comprises at least one active principle.

\* \* \* \* \*